US010438692B2

(12) United States Patent
Neff

(10) Patent No.: US 10,438,692 B2
(45) Date of Patent: Oct. 8, 2019

(54) PRIVACY PROTECTION BASED ON DEVICE PRESENCE

(71) Applicant: Cerner Innovation, Inc., Kansas City, KS (US)

(72) Inventor: Robert A Neff, Villanova, PA (US)

(73) Assignee: Cerner Innovation, Inc., Kansas City, KS (US)

( * ) Notice: Subject to any disclaimer, the term of this patent is extended or adjusted under 35 U.S.C. 154(b) by 156 days.

(21) Appl. No.: 14/220,175

(22) Filed: Mar. 20, 2014

(65) Prior Publication Data
US 2015/0269318 A1    Sep. 24, 2015

(51) Int. Cl.
*G16H 10/60*    (2018.01)

(52) U.S. Cl.
CPC .................................. *G16H 10/60* (2018.01)

(58) Field of Classification Search
CPC ........ G06Q 50/22; G06Q 50/24; G16H 10/60; G06F 19/3462
USPC ............................................................ 705/3
See application file for complete search history.

(56) References Cited

U.S. PATENT DOCUMENTS

| | | |
|---|---|---|
| 4,857,716 A | 8/1989 | Gombrich et al. |
| 5,482,050 A | 1/1996 | Smokoff et al. |
| 5,786,850 A | 7/1998 | Pritchett et al. |
| 5,798,798 A | 8/1998 | Rector et al. |
| 5,915,379 A | 6/1999 | Wallace et al. |
| 5,942,986 A | 8/1999 | Shabot et al. |
| 6,050,940 A | 4/2000 | Braun et al. |
| 6,095,984 A | 8/2000 | Amano et al. |
| 6,174,283 B1 | 1/2001 | Nevo et al. |
| 6,188,407 B1 | 2/2001 | Smith et al. |
| 6,269,812 B1 | 8/2001 | Wallace et al. |
| 6,287,452 B1 | 9/2001 | Allen et al. |
| 6,322,502 B1 | 11/2001 | Schoenberg et al. |
| 6,369,838 B1 | 4/2002 | Wallace et al. |
| 6,429,869 B1 | 8/2002 | Kamakura et al. |
| 6,804,656 B1 | 10/2004 | Rosenfeld et al. |
| 7,323,991 B1 | 1/2008 | Eckert et al. |
| 7,612,679 B1 | 11/2009 | Fackler et al. |
| 7,634,419 B1 | 12/2009 | Travis et al. |

(Continued)

FOREIGN PATENT DOCUMENTS

DE    198 44 918 A1    9/1998

OTHER PUBLICATIONS

Tom Mooney, "Rhode Island ER first to test Google Glass on medical conditions", http://www.ems1.com/ems-products/cameras-video/articles/1860487-Rhode-Island-ER-first . . . printed on Mar. 11, 2014.

(Continued)

*Primary Examiner* — Hiep V Nguyen
(74) *Attorney, Agent, or Firm* — Shook, Hardy & Bacon L.L.P.

(57) ABSTRACT

Disclosed herein is a framework for facilitating privacy protection based on device presence. In accordance with one aspect, presence of a recording device is determined. A set of one or more privileges associated with the recording device may be retrieved. Based on the set of one or more privileges, the framework may control acquisition of personal health information (PHI) by the recording device, wherein the PHI is accessible via a PHI presentation device that is within a predetermined distance from the recording device.

18 Claims, 3 Drawing Sheets

(56) References Cited

U.S. PATENT DOCUMENTS

| | | |
|---|---|---|
| 7,756,723 B2 | 7/2010 | Rosow et al. |
| 7,945,457 B2 | 5/2011 | Zaleski |
| 8,237,558 B2 | 8/2012 | Syed Momen et al. |
| 8,273,018 B1 | 9/2012 | Fackler et al. |
| 8,432,263 B2 | 4/2013 | Kunz |
| 2002/0015034 A1 | 2/2002 | Malmborg |
| 2002/0077863 A1 | 6/2002 | Rutledge et al. |
| 2002/0082867 A1 | 6/2002 | MacCarter et al. |
| 2002/0183976 A1 | 12/2002 | Pearce |
| 2003/0037786 A1 | 2/2003 | Biondi et al. |
| 2003/0070177 A1 | 4/2003 | Kondo et al. |
| 2003/0092974 A1 | 5/2003 | Santoso et al. |
| 2003/0095147 A1 | 5/2003 | Daw |
| 2003/0140928 A1 | 7/2003 | Bui et al. |
| 2003/0227386 A1 | 12/2003 | Pulkkinen et al. |
| 2004/0019900 A1 | 1/2004 | Knightbridge et al. |
| 2004/0054760 A1 | 3/2004 | Ewing et al. |
| 2004/0116804 A1 | 6/2004 | Mostafavi |
| 2004/0193449 A1 | 9/2004 | Wildman et al. |
| 2005/0038326 A1 | 2/2005 | Manthur |
| 2005/0228245 A1 | 10/2005 | Quy |
| 2005/0249139 A1 | 11/2005 | Nesbit |
| 2006/0004606 A1 | 1/2006 | Wendl et al. |
| 2006/0089541 A1 | 4/2006 | Braun et al. |
| 2006/0092043 A1 | 5/2006 | Lagassey |
| 2006/0107295 A1 | 5/2006 | Margis et al. |
| 2006/0206011 A1 | 9/2006 | Higgins et al. |
| 2006/0246921 A1 | 11/2006 | Russ |
| 2006/0259326 A1 | 11/2006 | Ambekar et al. |
| 2006/0279427 A1 | 12/2006 | Becker et al. |
| 2007/0033073 A1 | 2/2007 | Tajaliawal et al. |
| 2007/0156456 A1 | 7/2007 | McGillin et al. |
| 2007/0162304 A1 | 7/2007 | Rodgers |
| 2007/0180047 A1 | 8/2007 | Dong et al. |
| 2007/0183493 A1 | 8/2007 | Kimpe |
| 2007/0192133 A1 | 8/2007 | Morgan |
| 2007/0255348 A1 | 11/2007 | Holtzclaw |
| 2008/0004904 A1* | 1/2008 | Tran ............... A61B 5/0006 705/2 |
| 2008/0068447 A1 | 3/2008 | Mattila et al. |
| 2008/0123750 A1 | 5/2008 | Bronstein et al. |
| 2008/0125288 A1 | 5/2008 | Case |
| 2008/0147442 A1 | 6/2008 | Warner et al. |
| 2008/0204236 A1 | 8/2008 | Kraft-Oz |
| 2008/0221928 A1 | 9/2008 | Garcia et al. |
| 2008/0243896 A1 | 10/2008 | Sitomer et al. |
| 2008/0249376 A1 | 10/2008 | Zaleski |
| 2008/0249801 A1 | 10/2008 | Zaleski |
| 2009/0054735 A1 | 2/2009 | Higgins et al. |
| 2009/0062626 A1 | 3/2009 | Baldus et al. |
| 2009/0206992 A1* | 8/2009 | Giobbi ............... G06Q 10/10 340/5.74 |
| 2009/0231124 A1 | 9/2009 | Klabunde et al. |
| 2009/0287837 A1* | 11/2009 | Felsher ............... G06F 19/322 709/229 |
| 2010/0292556 A1* | 11/2010 | Golden ............... A61B 5/7465 600/364 |
| 2011/0047628 A1* | 2/2011 | Viars ............... G06F 19/322 726/28 |
| 2011/0105854 A1* | 5/2011 | Kiani ............... G06F 19/327 600/300 |
| 2013/0085764 A1 | 4/2013 | Sawka |
| 2013/0085776 A1 | 4/2013 | Sawka |
| 2014/0114681 A1 | 4/2014 | Eaton et al. |
| 2014/0114688 A1 | 4/2014 | Eaton et al. |
| 2014/0207686 A1* | 7/2014 | Experton ............ G06F 19/3418 705/51 |

OTHER PUBLICATIONS

Non-Final Office Action dated Aug. 5, 2016 in U.S. Appl. No. 12/062,631, 16 pages.

* cited by examiner

PRIVACY PROTECTION BASED ON DEVICE PRESENCE

TECHNICAL FIELD

The present disclosure generally relates to systems and methods for privacy protection based on device presence.

BACKGROUND

Medical privacy, also known as health privacy, is the practice of keeping information about a patient confidential. In the modern electronic age, this typically involves the security of medical records stored in health information systems. Another aspect of medical privacy involves the physical privacy of patient health information from third parties (e.g., other patients, providers, etc.) in a medical facility. With the proliferation of mobile recording devices (e.g., smartphone, tablets, wearable computers, etc.) equipped with, for example, a microphone and/or camera, new concerns are raised about inadvertently disclosing sensitive patient information to unauthorized third parties with such devices in the vicinity.

SUMMARY

The present disclosure relates to a framework for facilitating privacy protection based on device presence. In accordance with one aspect, presence of a recording device is determined. A set of one or more privileges associated with the recording device may be retrieved. Based on the set of one or more privileges, the framework may control acquisition of personal health information (PHI) by the recording device, wherein the PHI is accessible via a PHI presentation device that is within a predetermined distance from the recording device.

This summary is provided to introduce a selection of concepts in a simplified form that are further described below in the following detailed description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings. Furthermore, it should be noted that the same numbers are used throughout the drawings to reference like elements and features.

DETAILED DESCRIPTION

Figure 1:
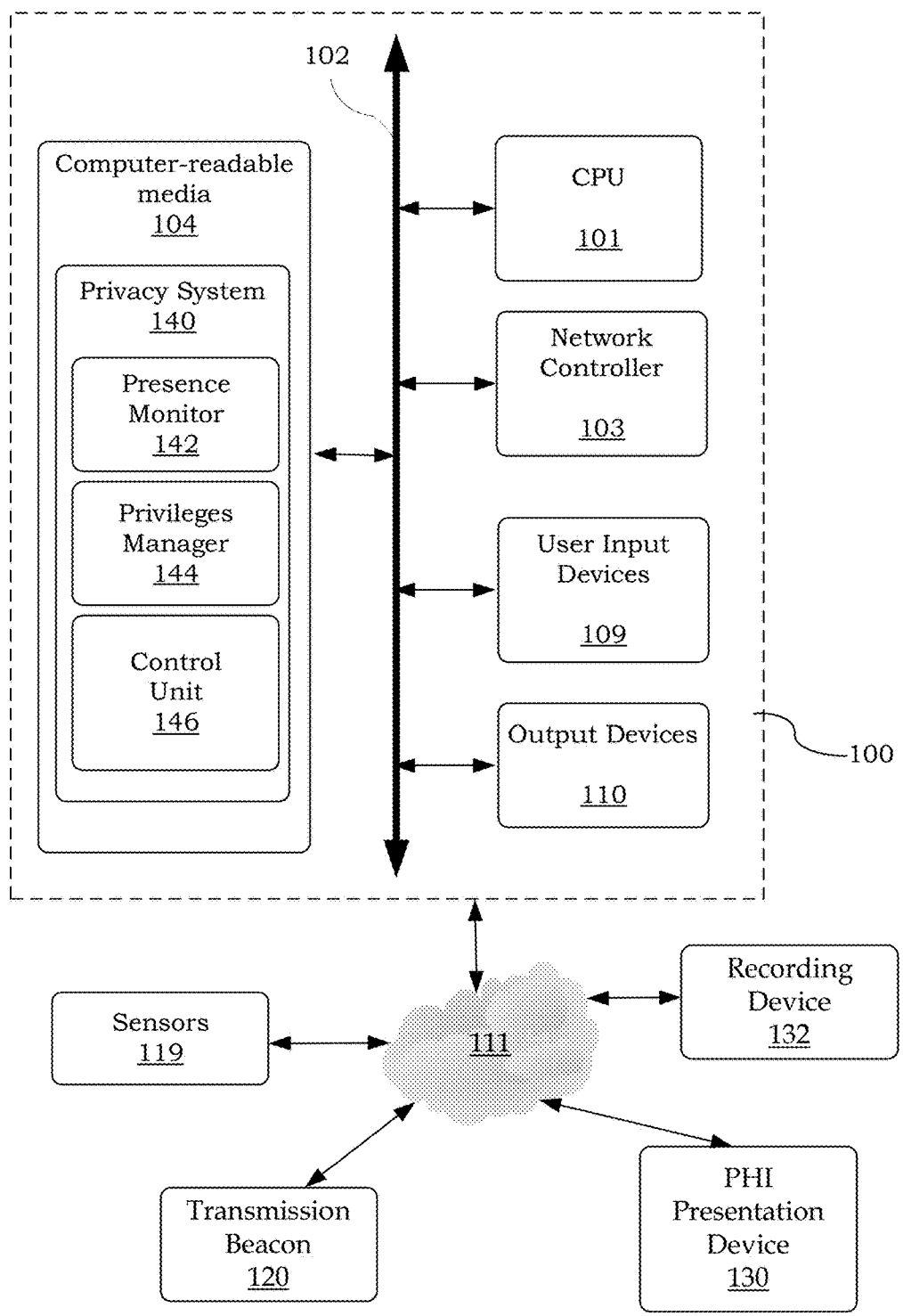
FIG. 1 shows an exemplary architecture.

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

It is to be understood that the system and methods described herein may be implemented in various forms of hardware, software, firmware, special purpose processors, or a combination thereof. Preferably, the present invention is implemented in software as an application (e.g., n-tier application) comprising program instructions that are tangibly embodied on one or more non-transitory program storage devices (e.g., magnetic floppy disk, RAM, CD ROM, ROM, etc.), and executable by any device or machine comprising suitable architecture. If written in a programming language conforming to a recognized standard, sequences of instructions designed to implement the methods can be compiled for execution on a variety of hardware platforms and for interface to a variety of operating systems. In addition, embodiments of the present framework are not described with reference to any particular programming language. It will be appreciated that a variety of programming languages may be used to implement embodiments of the present invention.

It is to be further understood that since at least a portion of the constituent system modules and method steps depicted in the accompanying Figures may be implemented in software, the actual connections between the system components (or the flow of the process steps) may differ depending upon the manner in which the present invention is programmed. Given the teachings herein, one of ordinary skill in the related art will be able to contemplate these and similar implementations or configurations of the present invention.

The present disclosure describes a framework (e.g., system) that facilitates privacy protection based on device presence. In accordance with one aspect, a privacy framework is provided to prevent non-authorized recording devices (e.g., smartphones, mobile phones, wearable computers, etc.) from acquiring personal health information (PHI). Personal health information (PHI), also referred to as protected health information, generally refers to demographic information (e.g., age, gender, etc.), medical history, test and laboratory results, insurance information and other data that is collected by a healthcare professional to identify an individual and determine appropriate care.

Components of the present framework may cooperate with recording devices and/or PHI presentation devices to ensure privacy of patients is respected. In some implementations, visual and/or auditory privacy of PHI is protected. In medical facilities, for example, healthcare providers (e.g., nurses, doctors, etc.) may access a patient's PHI via a PHI presentation device (e.g., laptop or terminal), which may expose the patient's PHI to unintended viewing, hearing and/or recording by unauthorized passers-by with recording devices, particularly in high traffic public areas. The present framework may serve to preserve the privacy of sensitive PHI while it is entered, presented or used at PHI presentation devices that are within predetermined distances from recording devices. These exemplary advantages and features will be described in more detail in the following description.

FIG. 1 shows an exemplary computer system for implementing a method and system of the present disclosure. The computer system referred to generally as system 100 may include, inter alia, a processor such as a central processing unit (CPU) 101, a non-transitory computer-readable media 104, a network controller 103, an internal bus 102, one or more user input devices 109 (e.g., keyboard, mouse, touch screen, etc.) and one or more output devices 110 (e.g., printer, monitor, external storage device, etc.). Computer system 100 may further include support circuits such as a cache, a power supply, clock circuits and a communications bus. The computer system 100 may take the form of hardware, software, or may combine aspects of hardware and software. Although the computer system 100 is represented by a single computing device in FIG. 1 for purposes of illustration, the operation of the computer system 100 may be distributed among a plurality of computing devices. For example, it should be appreciated that various subsystems (or portions of subsystems) of the computer system 100 may operate on different computing devices. In some such implementations, the various subsystems of the system 100 may communicate over the network 111.

The network 111 may be any type of communication scheme that allows computing devices to exchange data. For example, the network 111 may include fiber optic, wired, and/or wireless communication capability in any of a plurality of protocols, such as TCP/IP, Ethernet, WAP, IEEE 802.11, or any other protocol. Implementations are contemplated in which the system 100 may be accessible through a shared public infrastructure (e.g., Internet), an extranet, an intranet, a virtual private network ("VPN"), a local area network (LAN), a wide area network (WAN), P2P, a wireless communications network, or any combination thereof.

The computer system 100 may cooperate with external components via the network 111. In some implementations, computer system 100 is communicatively coupled to sensors 119, such as image sensor (e.g., camera), audio sensor (e.g., microphone), signal detector (e.g., Wi-Fi, Bluetooth, Radio-frequency identification or RFID signal detector), positioning sensors (e.g., proximity sensor, global positioning system or GPS receiver, indoor positioning system or IPS receiver, etc.), and so forth. Such sensors 119 may be standalone, or incorporated in PHI presentation device 130 and/or recording device 132.

In some implementations, computer system 100 is communicatively coupled to transmission beacon 120, which is configured to wirelessly transmit signals to, for example, PHI presentation device 130, recording device 132, or any other devices accessible via network 111. Computer system 100 may also transmit such signals directly to the network devices via wired connections.

Personal health information (PHI) presentation device 130 generally refers to any output device that can be used to access (e.g., visual display, enter, hear, print, etc.) personal health information. Examples of PHI presentation device 130 include, for example, monitor, printer, touch screen, speaker, projector, speaker, laptop, computer, client terminal, and so forth. The PHI presentation device 130 may also be a medical device with an integrated output device (e.g., medical monitor with integrated display component). PHI may be manually entered into, or stored locally at, the PHI presentation device 130. PHI presentation device 130 may also retrieve PHI of a patient from, for example, a database structured to store data relating to the healthcare of patients, such as individual health records.

Recording device 132 generally refers to any input device that can acquire PHI from the PHI presentation device 130. In some implementations, recording device 132 is capable of capturing images or video of PHI while it is in plain view or sight at the PHI presentation device 130. Examples of recording devices 132 include, but are not limited to, cameras, video recorders, audio recorders, mobile recording devices (e.g., smartphones, tablets, etc.), wearable computers (e.g., Google Glass, EyeTap, Golden-i, etc.), and so forth. Such recording devices may be physically hand-held, worn, carried or otherwise possessed by, for example, patients, healthcare providers, employees, visitors and/or other third parties in a healthcare facility.

The present technology may be implemented in various forms of hardware, software, firmware, special purpose processors, or a combination thereof, either as part of the microinstruction code or as part of an application program or software product, or a combination thereof, which is executed via the operating system. In some implementations, the techniques described herein may be implemented as computer-readable program code tangibly embodied in non-transitory computer-readable media 104. Non-transitory computer-readable media 104 may include one or more memory storage devices such as random access memory (RAM), read only memory (ROM), magnetic floppy disk, flash memory, and other types of memories, or a combination thereof.

The present techniques may be implemented by a privacy system 140 that is stored in computer-readable media 104. In some implementations, privacy system 140 serves to facilitate privacy protection of PHI presented by PHI presentation device 130 in the presence of recording devices 132. Privacy system 140 may include a presence monitor 142, a privileges manager 144 and an control unit 146. It should be understood that less or additional components may be included in the privacy system 140, and the privacy system 140 is not necessarily implemented in a single computer system.

In accordance with some implementations, privacy system 140 operates as an opt-in system. In an opt-in system, privacy system 140 may certify recording devices 132 that comply with a standard privacy protocol of the privacy system 140. Only certified recording devices 132 may be allowed to be physically carried by their users into a healthcare facility. Non-certified recording devices may be deactivated and/or held in, for example, custodial care at the reception area or any other area. The recording devices 132 may be certified at the time of manufacture or any other suitable time. Additionally, the recording devices 132 may display an indication (e.g., logo, sign, text, etc.) or may otherwise be recognized to respect the standard privacy protocol associated with the privacy system 140.

Privacy system 140 may allow specific devices to be registered. Privacy system 140 may communicate signals, via the network 111, to registered recording devices 132 to override general lockouts in the devices. This allows it to, for example, control (e.g., block) the recording function of the device 132 or to modify (e.g., erase, selectively blank, etc.) the content of recorded data stored in or transmitted by the device 132.

Privacy system 140 may also operate as a non opt-in system. Recording devices 132 need not be certified by the privacy system 140 for their presence to be determined or detected. Privacy system 140 may automatically determine the presence of such recording devices 132 within the healthcare facility by, for example, detecting a wireless signal (e.g., Wifi, RFID, Bluetooth, infrared, ultrasonic signals, etc.) broadcast or transmitted by the recording devices 132, or by recognizing such devices 132 via automated recognition techniques (e.g., image recognition).

The computer system 100 may be a general purpose computer system that becomes a specific purpose computer system when executing the computer-readable program code. It is to be understood that, because some of the constituent system components and method steps depicted in the accompanying figures can be implemented in software, the actual connections between the systems components (or the process steps) may differ depending upon the manner in which the present framework is programmed. For example, the system 100 may be implemented in a client-server, peer-to-peer (P2P) or master/slave configuration. Given the teachings of the present disclosure provided herein, one of ordinary skill in the related art will be able to contemplate these and similar implementations or configurations of the present invention.

Figure 2:
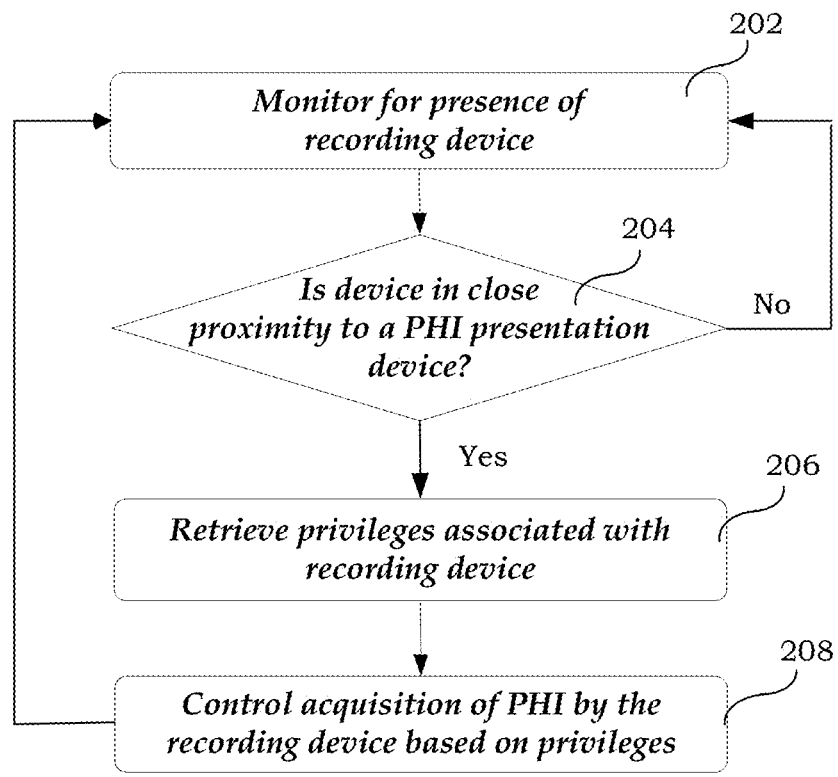
FIG. 2 is a flow diagram illustrating an exemplary privacy protection method.

FIG. 2 shows an exemplary method 200 of privacy protection. The steps of the method 200 may be performed in the order shown or a different order. Additional, different, or fewer steps may be provided. Further, the method 200 may be implemented with the system 100 of FIG. 1, a different system, or a combination thereof.

At 202, presence monitor 142 monitors the healthcare facility for the presence of a recording device 132. Various methods may be implemented to determine the presence of the recording device 132 in a healthcare facility (e.g., hospital, clinic, office, etc.). Privacy system 140 may determine presence of the recording device 132 based on, for instance, sensor data provided by sensors 119.

In some implementations, privacy system 140 employs automatic image recognition techniques to recognize the presence of a recording device 132. For example, privacy system 140 may detect, within a surveillance image or video, a privacy certification indicator (e.g., logo) displayed on the device 132, or visual characteristics (e.g., typical shape and size) distinctive of a recording device.

Privacy system 140 may also determine the presence of the recording devices 132 based on the signals they communicate. For example, in an opt-in scenario, certified recording devices may be required by the privacy protocol to transmit a signal to, for example, a nearby PHI presentation device 130, to indicate that it is present and PHI visual access control should be invoked. In a non opt-in scenario, privacy system 140 may passively determine the recording devices 132 without requiring them to register with the privacy system 140 by, for example, detecting wireless signals that are typically broadcast or transmitted by such devices to, for example, communicate with other devices (e.g., Wifi, RFID, Bluetooth, infrared, ultrasonic signals, etc.).

At 204, presence monitor 142 determines if the recording device 132 is within a predetermined distance (i.e., in close proximity) to a PHI presentation device 130. Such distance may be predetermined based on, for example, a typical visual range of an unaided eye or a camera. In some implementations, presence monitor 142 determines the location of the detected recording device 132 based on positioning data provided by positioning sensors 119. Presence monitor 142 may compare the location of the detected recording device 132 with the locations of PHI presentation device 130 within the healthcare facility to determine if the recording device 132 is within a predetermined distance from any PHI presentation device 130. Alternatively, or additionally, each PHI presentation device 130 may be equipped with sensors 119 to determine the proximity of a recording device and to transmit a signal to the privacy system 140 in response to such determination. If a particular recording device 132 is determined to be within the predetermined distance of a particular PHI presentation device 130, the process 200 continues to step 206. If not, the process 200 repeats at step 202.

At 206, privileges manager 144 retrieves a set of privileges (or permissions) associated with the recording device 132. Such privileges may define permissions to access (e.g., view, hear, acquire, etc.) PHI associated with a particular patient. For example, a regular visitor in a hospital may have his or her recording device 132 restricted from acquiring any data, while a healthcare provider may be allocated with recording privileges. As another example, the PHI presentation device 130 may blank out display of PHI associated with the patient when an unauthorized third party with the recording device 132 is within close proximity.

The set of privileges may be allocated according to the level of authorization of the user associated with the recording device 132. For example, a healthcare provider (e.g., physician, nurse) treating the patient associated with the PHI, or the patient herself, may be associated with the highest level of authorization and therefore be associated with privileges to access the PHI. A visitor, neighboring patient, passer-by or any other third party who is not authorized to view PHI of the particular patient, may be associated with the lowest level of authorization and therefore be denied privileges to access the PHI. The level of authorization, or privileges associated therewith, may be pre-defined by the system 100 and/or customized by the patient. For example, privileges manager 144 may maintain a whitelist of devices using, for example, media access control (MAC) addresses or other unique identifier, that are associated with privileges to access the PHI. The patient may also designate particular users (e.g., relatives) to be authorized to access his or her PHI.

In some implementations, privileges manager 144 defines the privileges based on location data and/or time data. For example, the privileges associated with the recording devices 132 of a healthcare provider (e.g., physician) may permit access to PHI within the GPS latitude and longitude zone of the healthcare facility. Recording devices 132 associated with other users may be, for example, disabled or restricted.

At 208, control unit 146 controls the acquisition of PHI by the recording device 132 based on the set of privileges. Such PHI includes patient-identifying information, such as name, patient number, social security number, unique identifier, account number, date of birth, address, contact information, photograph, etc. The acquisition of PHI may be controlled by various exemplary approaches. One exemplary approach seeks to indirectly control the acquisition of PHI by restricting the exposure or visibility of PHI at the PHI presentation device 130. Another exemplary approach seeks to directly control the acquisition of PHI by controlling the recording device 132 itself or the data acquired by the recording device 132.

More particularly, under the indirect control approach, control unit 146 may control the presentation of PHI based on the set of privileges. Control unit 146 may communicate a control signal to the appropriate PHI presentation device 130 to control the presentation of PHI. In response to the control signal, PHI presentation device 130 may block the presentation (e.g., display) or selectively blank out, obscure, obfuscate or blur PHI data.

Figure 3:
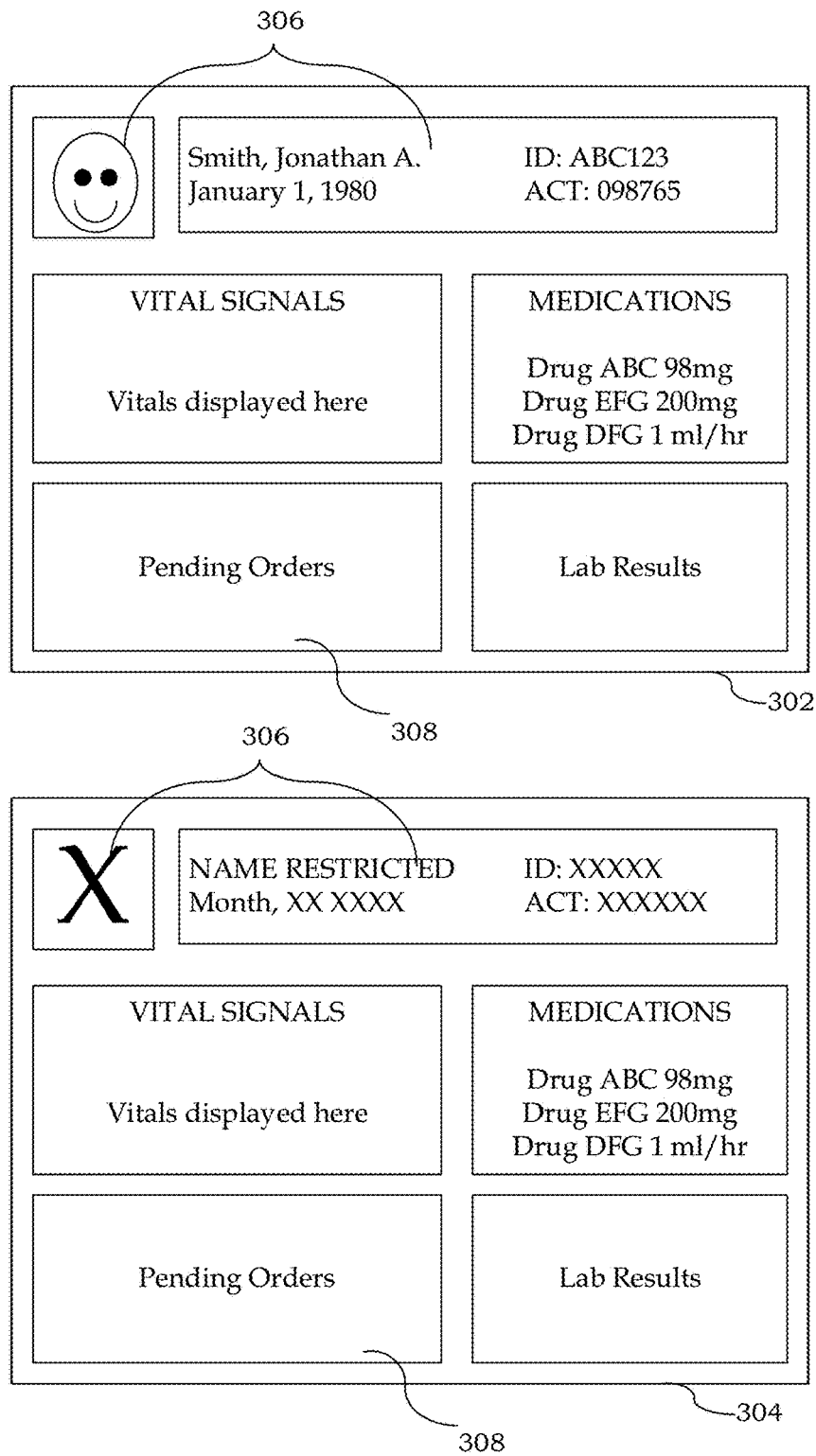
FIG. 3 shows exemplary screens displayed by a personal health information presentation device.

FIG. 3 shows an exemplary regular screen 302 and an exemplary restricted screen 304 displayed by a PHI presentation device 130. The exemplary regular screen 302 may display all types of information, including PHI 306 (e.g., photo, name, identifier, birth date, account number, etc.) and other patient information 308 (e.g., vital signs, medications, pending order, lab results, etc.). The regular screen 302 may be presented in the presence of, for example, users of recording devices 132 associated with PHI access privileges (e.g., physicians, nurses, etc.).

The exemplary restricted screen 304, however, displays only patient information 308. PHI information 306 is selectively blanked out by replacing them with predefined characters (e.g., "X" characters). The restricted screen 304 may be presented in the presence of, for example, users of recording devices 132 associated with no PHI access privileges (e.g., unauthorized third parties).

Under the direct control approach, control unit 146 may directly control the recording device 132. This step may be implemented in an opt-in system which allows recording devices 132 to be registered and general lockouts of the devices 132 to be overridden. In some implementations, acquisition of PHI may be controlled by controlling a recording function of the recording device 132. Control unit 146 may communicate a control signal to the appropriate recording device 132 to completely or partially disable any recording function for a predetermined period of time. For example, the recording function may be delayed by the first X milliseconds (i.e. recording lag), such that any PHI data that is automatically recognized by image recognition techniques as such is not captured as part of the recording.

Additionally, or alternatively, control unit 146 may filter any recorded PHI based on the associated privileges. In some implementations, control unit 146 may selectively remove, subtract or obfuscate any recorded PHI from the recorded data stored on, or communicated by, the recording device 132. For instance, any PHI data recorded by a camera of the recording device 132 may be recognized using image recognition techniques and removed (e.g., blurred or blanked out) from the recorded data.

While the present invention has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

The invention claimed is:

1. A system for facilitating privacy protection, comprising:
   a non-transitory memory device for storing computer readable program code; and
   a processor in communication with the memory device, the processor being operative with the computer readable program code to:
   automatically determine, by a privacy system comprising a presence monitor, the presence of a recording device by continuously monitoring a healthcare facility for detectable wireless signals communicated by the recording device to one or more sensors of the presence monitor, wherein the recording device comprises one or more general lockouts;
   detect, by the presence monitor, at least one wireless signal from the recording device and automatically determine that the recording device is within a predetermined distance from a personal health information (PHI) presentation device, based on a received distance threshold, wherein the one or more general lockouts of the recording device are overridden based on the at least one wireless signal and the determination that the recording device is within the predetermined distance from the PHI presentation device;
   retrieve, by a privileges manager in communication with the privacy system based on the detected at least one wireless signal from the recording device that is determined to be within the predetermined distance from the PHI presentation device, a set of one or more privileges associated with the recording device, the one or more privileges defining an access permission for PHI associated with a particular patient, wherein the privileges manager associates the one or more privileges to the recording device and the particular patient; and
   automatically control acquisition of PHI by the recording device via a control unit of the privacy system, the acquisition control enabled by the control unit generating a wireless control signal based at least on the set of one or more privileges and transmitting the wireless control signal to at least one of the recording device and the presentation device, wherein the PHI is accessible via a PHI presentation device that is within the predetermined distance from the recording device.

2. The system of claim 1 wherein the recording device comprises a smartphone or tablet.

3. The system of claim 1 wherein the recording device comprises a wearable computer.

4. The system of claim 1 wherein the processor is further operative with the computer readable program code to register the recording device to override general lockouts in the recording device.

5. The system of claim 1 wherein the recording device is certified to comply with a standard privacy protocol.

6. The system of claim 1 wherein the processor is operative with the computer readable program code to determine presence of the recording device by performing an image recognition technique to recognize the recording device in surveillance image or video.

7. The system of claim 1 wherein the processor is further operative with the computer readable program code to maintain a whitelist of devices that are associated with one or more privileges to access the PHI.

8. The system of claim 1 wherein the processor is further operative with the computer readable program code to define at least one of the set of one or more privileges based on location data, time data or a combination thereof.

9. The system of claim 1 wherein the processor is operative with the computer readable program code to control acquisition of the PHI by controlling the recording device.

10. The system of claim 9 wherein the processor is operative with the computer readable program code to control the recording device by transmitting the wireless control signal to the recording device and causing the recording device to disable the recording function.

11. The system of claim 1 wherein the processor is operative with the computer readable program code to control acquisition of the PHI by selectively removing or obfuscating any PHI data recorded by the recording device.

12. The system of claim 1 wherein the processor is operative with the computer readable program code to control acquisition of the PHI via the control unit, by controlling presentation of the PHI by the PHI presentation device based on the wireless control signal.

13. The system of claim 12 wherein the processor is operative with the computer readable program code to control the presentation of the PHI by transmitting the wireless control signal to the PHI presentation device and causing the PHI presentation device to selectively blank out the PHI data.

14. A non-transitory computer readable medium embodying a program of instructions executable by machine to perform steps for facilitating privacy protection, the steps comprising:
   automatically determining, by a privacy system comprising a presence monitor, the presence of a recording device by continuously monitoring a healthcare facility for detectable signals communicated by the recording device to one or more sensors of the presence monitor, wherein the recording device comprises one or more general lockouts;
   detecting, by the presence monitor, at least one signal from the recording device and automatically determining that the recording device is within a predetermined distance from a personal health information (PHI) presentation device, based on a received distance threshold, wherein the one or more general lockouts of the recording device are overridden based on the at least one wireless privacy signal and the determination that the recording device is within the predetermined distance from the PHI presentation device;
   retrieving, by a privileges manager in communication with the privacy system based on the detected at least one wireless signal from the recording device that is determined to be within the predetermined distance from the PHI presentation device, a set of one or more privileges associated with the recording device, the one or more privileges defining an access permission for PHI associated with a particular patient, wherein the privileges manager associates the one or more privileges to the recording device and the particular patient; and
   automatically controlling acquisition of PHI by the recording device via a control unit of the privacy system, the control unit generating a wireless control signal based at least on the set of one or more privileges and transmitting the wireless control signal to at least one of: the recording device to control a recording function and the presentation device to control the presentation of the PHI, wherein the PHI is accessible via a PHI presentation device that is within the predetermined distance from the recording device.

15. A method of privacy protection, comprising:
   automatically determining, by a privacy system comprising a presence monitor, the presence of a recording device by continuously monitoring for detectable signals communicated by the recording device to one or more sensors of the presence monitor, wherein the recording device comprises one or more general lockouts;
   detecting, by the presence monitor, at least one signal from the recording device and automatically determining that the recording device is within a predetermined distance from a personal health information (PHI) presentation device, based on a received distance threshold, wherein the one or more general lockouts of the recording device are overridden based on the at least one wireless privacy signal and the determination that the recording device is within the predetermined distance from the PHI presentation device;
   retrieving, by a privileges manager in communication with the privacy system based on the detected at least one wireless signal from the recording device that is determined to be within the predetermined distance from the PHI presentation device, a set of one or more privileges associated with the recording device, the one or more privileges defining an access permission associated with PHI corresponding to a particular patient, wherein the privileges manager associates the one or more privileges to the recording device and the particular patient; and
   automatically controlling the acquisition of PHI by the recording device via a control unit of the privacy system, the control unit generating a wireless control signal based at least on the set of one or more privileges and transmitting the wireless control signal to at least one of the recording device and the presentation device, wherein the PHI is accessible via a PHI presentation device that is within the predetermined distance from the recording device.

16. The method of claim 15 wherein controlling acquisition of the PHI comprises controlling a recording function of the recording device.

17. The method of claim 15 wherein controlling acquisition of the PHI comprises controlling presentation of the PHI by the PHI presentation device.

18. The method of claim 15 wherein controlling acquisition of the PHI comprises selectively removing or obfuscating any PHI data recorded by the recording device.

* * * * *